United States Patent [19]

Niizuma et al.

[11] Patent Number: 4,677,225
[45] Date of Patent: Jun. 30, 1987

[54] PROCESS FOR THE PRODUCTION OF ACRYLIC ACID OR METHACRYLIC ACID

[75] Inventors: Hiroshi Niizuma, Aichi; Toshiro Miki, Tokyo; Shiro Kojima, Aichi; Kishiro Azuma, Aichi; Hiroyuki Kato, Aichi; Yuichi Murakami, Aichi; Tsutomu Ito, Tokyo, all of Japan

[73] Assignee: Toagosei Chemical Industry Co., Ltd., Tokyo, Japan

[21] Appl. No.: 736,621

[22] Filed: May 21, 1985

[30] Foreign Application Priority Data

May 21, 1984 [JP] Japan ................................. 59-100418
Nov. 13, 1984 [JP] Japan ................................. 59-237507
Apr. 3, 1985 [JP] Japan ................................. 60-69179

[51] Int. Cl.$^4$ ...................... C07C 51/353; C07C 57/04
[52] U.S. Cl. ......................................... 562/599; 560/214
[58] Field of Search ........................ 562/599; 560/214

[56] References Cited

U.S. PATENT DOCUMENTS

| | | | |
|---|---|---|---|
| 2,734,074 | 2/1956 | Redmon | 560/210 |
| 3,014,958 | 12/1961 | Koch et al. | 560/210 |
| 3,051,747 | 8/1962 | Leathers et al. | 562/599 |
| 3,532,740 | 10/1970 | Hargis et al. | 560/214 |
| 4,165,438 | 8/1979 | Schneider | 560/211 |
| 4,339,598 | 7/1982 | Guttmann et al. | 560/210 |
| 4,490,476 | 12/1984 | Piccolini et al. | 502/203 |

Primary Examiner—Werren B. Lone
Attorney, Agent, or Firm—Sughrue, Mion, Zinn, Macpeak, and Seas

[57] ABSTRACT

A process for producing acrylic acid or methacrylic acid by reacting acetic acid or propionic acid with formaldehyde in a gas phase is described, characterized by carrying out the reaction in the presence of a solid catalyst containing at least one of boron oxide or phosphorus oxide and having an acid site of an acid strength, $pKa \leq -3.0$. The solid catalyst is of high activity and is satisfactory in both selectivity and conversion and, furthermore, its high selectivity can be maintained for long periods of time. Thus the desired product, acrylic acid or methacrylic acid, can be produced in high yield.

16 Claims, 1 Drawing Figure

PROCESS FOR THE PRODUCTION OF ACRYLIC ACID OR METHACRYLIC ACID

FIELD OF THE INVENTION

The present invention relates to a process for the production of acrylic acid or methacrylic acid. More particularly, it is concerned with a process for producing acrylic acid or methacrylic acid by reacting acetic acid or propionic acid with formaldehyde in a gas phase in the presence of a solid catalyst.

BACKGROUND OF THE INVENTION

A process of production of acrylic acid or methacrylic acid through dehydration-condensation of acetic acid or propionic acid and formaldehyde is well known in the art, and the following have been proposed as useful catalysts.

Examples of catalysts include a basic catalyst such as a catalyst comprising an alkali or alkaline earth metal hydroxide carried on alumina silicate or silica gel (Japanese Patent Publication No. 21928/70), a basic catalyst comprising calcined silica (Japanese Patent Application (OPI) No. 70919/74 (the term "OPI" as used herein means a "published unexamined Japanese patent application")), a basic catalyst having a great surface area (Japanese Patent Publication No. 40130/82), a catalyst comprising an alkali metal carboxylate carried on active alumina (U.S. Pat. No. 3,051,747), a catalyst comprising a metaphosphoric acid alkali metal or alkaline earth metal salt carried on silica gel (Japanese Patent Publication No. 16728/71), and an aluminosilicate catalyst containing an alkali metal or alkaline earth metal salt (U.S. Pat. No. 3,247,248), a phosphate-based catalyst (Japanese Patent Application (OPI) No. 123137/82), a vanadium-antimony catalyst (Japanese Patent Application (OPI) No. 123138/82), a vanadium orthophosphate catalyst (U.S. Pat. No. 4,165,438), etc.

Most of the known catalysts are basic catalysts or catalysts containing a basic component. The reason for this is that the dehydration-condensation reaction of acetic acid or propionic acid with formaldehyde is believed to proceed following a similar mechanism to that of the Claisen condensation occurring in the presence of a strong base.

Claisen Condensation Reaction (wherein R, R', and R" are each a hydrogen atom or an alkyl group).

In addition, a process utilizing synthetic crystalline aluminosilicates which are considered to belong to the group of solid acid catalysts has recently been proposed (see European Patent Laid-Open No. 122782).

These known catalysts, however, are not sufficiently satisfactory for practical use. Many of the catalysts are not always sufficiently satisfactory in the yield of the desired product; that is, selectivity is not sufficiently high, or even though selectivity is high, conversion is low. Some catalysts are relatively high in the yield but only at earlier stages of the reaction; that is, the high yield cannot be maintained for long periods of time and their service life is poor.

SUMMARY OF THE INVENTION

A object of the present invention is to provide a process for producing acrylic acid or methacrylic acid which comprises reacting acetic acid or propionic acid with formaldehyde in a gas phase in the presence of a catalyst, wherein the catalyst is a solid catalyst containing at least one of boron oxide and phosphorus oxide and having an acid site of acid strength, $pKa \leq -3.0$.

As a result of extensive investigations on various solid catalysts having an acid site for the production of acrylic acid or methacrylic acid through the reaction of propionic acid or acetic acid with formaldehyde, the following have been found.

(1) A solid catalyst containing at least one of boron oxide and phosphorus oxide and having an acid site of moderately high acid strength is useful. This solid catalyst has high activity and, in particular, greatly improved selectivity. Thus the desired product can be produced in high yield.

(2) The high selectivity can be maintained over a long period of time if steam is added to the reaction atmosphere. This greatly facilitates the separation of the desired product compared with the conventional processes.

(3) If an oxidation ability-retaining compound containing at least one of, (A) at least one of oxide of element selected from V, Cr, Co, Ni, Mo, W, Pb, and mixtures thereof and (B) at least one of heteropolyacid containing therein at least one of polyatom selected from V, Mo, W, and mixtures thereof is added to the solid catalyst, the yield of the desired product is more increased and the initial activity of the catalyst can be maintained even after a long period of time.

DETAILED DESCRIPTION OF THE INVENTION

Solid catalysts used in the present invention, containing at least one of boron oxide and phosphorus oxide and having an acid site of acid strength, $pKa \leq -3.0$, include catalysts prepared by adding at least one of boron oxide and phosphorus oxide to those generally called solid acid catalysts. The catalyst of the present invention is sufficient to contain at least one of boron oxide and phosphorus oxide and to have an acid site of acid strength, $pKa \leq -3.0$, although it is not limited to use such a solid acid catalyst.

The solid acid catalyst is generally believed to have a large number of weak base sites and a small number of strong acid sites on the surface thereof and to be nearly neutral as a whole.

The acid sites on the surface of the catalyst do not have the same acid strength but have varied degrees of acid strength; that is, it is believed that there is an acid strength distribution. The activity of the catalyst of the present invention is ascribable to the acid site having an acid strength of $pKa \leq -3.0$. The acid strength is represented in terms of pKa, and as the value of pKa is smaller (or the negative value is greater), the acid strength is stronger. The position of the acid site on the catalyst surface cannot be determined, but the amount of the acid site can be calculated from the amount of acid. In the present invention, the acid strength of the acid site and the acid amount are determined by the method described in Reference Example as described hereinafter, i.e., the titration analysis using an indicator which its color changes within a specific pKa range.

The solid catalyst of the present invention has an acid site having an acid strength of pKa ≦ −3.0. Catalysts having a decreased number of very weak acid sites having an acid strength of pKa > −3.0 or base sites are preferred. Catalysts not having such acid sites or base sites at all are more preferred. That is, those generally called solid base catalysts can be used as long as they have an acid site of acid strength, pKa ≦ −3.0, but solid acid catalysts are preferably used. The reason for this is that if there are many acid sites having an acid strength of pKa > −3.0, they may exert bad influences on the rearrangement reaction of the present invention.

The acid amount will hereinafter be explained. The acid amount can be deemed the amount of acid sites present on the catalyst surface. In general, as the value of the acid amount is greater, the catalytic activity per unit amount of the catalyst is higher. Thus, if the acid amount is small, a larger amount of the catalyst is needed to convert the same amount of the starting material, and the size of the reactor should be increased. This is disadvantageous from an economical standpoint.

In the present invention, acid sites having an acid strength of pKa ≦ −3.0 contribute to the reaction. Thus it is preferred that the amount of acids having an acid strength falling within the above-specified range is great. When the reaction of the present invention is carried out under conditions that the molar ratio of acetic acid or propionic acid to formaldehyde to be supplied, the rate of introduction of the mixed gas, and the reaction temperature fall within the preferred ranges as described hereinafter, catalysts in which the amount of acids having an acid strength of pKa ≦ −3.0 is at least 0.05 mmol per gram of the catalyst are preferred because they increase the conversion as well as the selectivity of the reaction. More preferred are catalysts in which the amount of acids having an acid strength of pKa ≦ −3.0 is 0.1 mmol or more per gram of the catalyst.

If, on the other hand, the acid strength of the acid site in the catalyst is too high, the selectivity of the reaction tends to drop. It is preferred in the present invention to use solid catalysts having an acid site of acid strength falling within the range of −11.35 ≦ pKa ≦ −3.0, with the range of −8.2 ≦ pKa ≦ −3.0 being more preferred.

The solid catalyst of the present invention is obtained by adding at least one of boron oxide and phosphorus oxide to a solid acid catalyst such as a catalyst containing as a major component an oxide or composite oxide of one or more of elements such as Si, Al, Ti, Zr, Cd, Sn, Ga, Y, and La, and zeolite, and has an acid strength of pKa ≦ −3.0.

In connection with the content of boron oxide or phosphorus oxide in the solid catalyst, it is preferred that the boron oxide content is from 1 to 50 wt %, and preferably from 5 to 30 wt % (calculated as $B_2O_3$), and the phosphorus oxide content is from 1 to 50 wt %, and preferably from 5 to 30 wt % (calculated as $P_2O_5$). Hereinafter all the percents are by weight unless otherwise indicated. Further all the proportion of phosphorus oxide and boron oxide are based on the total weight of the catalyst.

If the boron oxide or phosphorus oxide content is in excess of 50 wt %, it covers the catalyst surface as an inert substance. On the other hand, if it is less than 1 wt %, the acid strength and acid amount of the resulting catalyst are not sufficiently high. In either case, the activity is not increased sufficiently; in some cases, it drops.

Introduction of boron oxide or phosphorus oxide to solid acid catalysts such as those containing as a major component the oxide or composite oxide of one or more of elements such as Si, Al, Ti, Zr, Cd, Sn, Ga, Y, and La, and zeolites can be carried out by techniques such as an impregnation method in which the oxide or composite oxide is impregnated with an aqueous solution of the above additives, a kneading method in which a hydrogel or fine powder is mixed in a wet state, and a coprecipitation method in which the raw materials for the catalyst and the additive substances are gelled at the same time from a mixed aqueous solution thereof.

Raw materials for the boron oxide include boric acid, metaboric acid, and ammonium borate. Raw materials for the phosphorus oxide include phosphoric acid, pyrophosphoric acid, hypophosphorous acid, polyphosphoric acid, and ammonium phosphate.

Preferred in the present invention is a solid acid catalyst which the acid strength was increased by adding at least one of boron oxide and phosphorus oxide to the oxide of one or more of Si, Al, Ti, and Zr. A catalyst comprising silica alumina with boron oxide added thereto, and a catalyst comprising $TiO_2$ with both of boron oxide and phosphorus oxide added thereto are particularly preferred.

When, a suitable oxidation ability-retaining component, i.e., (A) at least one oxide of an element selected from V, Cr, Co, Ni, Mo, W, Pb, and mixtures thereof and/or (B) at least one heteropolyacid containing therein at least one polyatom selected from V, Mo, W, and mixtures thereof is added to the above solid acid catalyst, the yield of the desired product is increased and, furthermore, if the reaction is carried out in the presence of oxygen, the initial catalytic activity does not drop even after the reaction is carried out for a long period of time.

Though the reason for this is not clear, it is believed, that since the catalyst possesses an oxidation ability and the reaction is carried out in an oxidizing atmosphere, the deposition of carbonaceous residues on the surface of the catalyst responsible for low selectivity and deterioration of the activity can be prevented. In fact, after the reaction, the deposition of carbonaceous residues on the surface of the catalyst was hardly observed. The addition of the oxidation ability-retaining component is particularly effective for the following catalysts: a catalyst which the acid strength was increased by adding at least one of boron oxide and phosphorus oxide to the oxide of one or more of Si, Al, Ti, and Zr, and a catalyst comprising the oxide of Ti or composite oxide of Zr and Ti with boron oxide and/or phosphorus oxide added.

Heteropolyacids containing at least one of P, B, and Si as the heteroatom are more preferred in that the yield of the desired product is high.

The suitable oxidation ability-retaining component is as described above. In particular, one or more of the oxides of V, Cr, Co, Ni, and Mo, and heteropolyacids containing as a polyatom V or Mo are preferred.

If the amount of the oxidation ability-retaining component is too small, its oxidation ability is exhibited only insufficiently. On the other hand, if it is too large, the reaction which acetic acid or formaldehyde oxidizes into carbon monoxide and carbon dioxide is more predominant than the reaction of formation of acrylic acid or methacrylic acid. As a result, the selectivity of the desired product undesirably drops. Thus the preferred amount of the oxidation ability-retaining component being added is from 0.01 to 10 mmol, and more preferably from 0.03 to 5.0 mmol per gram of the catalyst (calculated as the metal of the oxidation ability-retaining component; in the case of the heteropolyacid, as the polyatom).

For the addition of the oxidation ability-retaining component, known techniques such as an impregnation method, a kneading method, and a coprecipitation method can be applied as in the case of the addition of the boron oxide or phosphorus oxide. In some cases, the oxidation ability-retaining component can be added simultaneously with the boron oxide or phosphorus oxide.

As raw materials, ammonium salts, chlorides, hydroxides, carbonates, and so on can be used.

As formaldehyde used in the present invention, not only formaldehyde itself but also formalin and polymers of formaldehyde such as trioxane and paraformaldehyde can be used. Thus the term "formaldehyde" as used herein includes all the compounds as described above.

The molar ratio of acetic acid or propionic acid/formaldehyde is preferably from 1/1 to 15/1. In a case that the polymer of formaldehyde is used as the raw material, it is calculated as the formaldehyde monomer. Hereinafter this is applicable all the cases in which the formaldehyde polymer is used.

If the molar ratio of acetic acid or propionic acid/formaldehyde is less than 1/1, decomposition of formaldehyde readily occurs. On the other hand, if it is in excess of 15/1, the loss of the acid component due to its decomposition is increased and, furthermore, the separation and recovery of the desired product from the reaction mixture becomes difficult.

The acid component and formaldehyde are supplied as a mixed gas, and the space velocity (hereinafter referred to as "SV") over the catalyst is preferably from 300 to 5,000 ml/hr/ml-Cat, and more preferably from 1000 to 4000 ml/hr/ml-cat. If the SV exceeds the upper limit, the conversion is decreased. On the other hand, if it is less than the lower limit, the selectivity is decreased.

The reaction temperature is preferably in the range of 200° to 500° C. If the reaction temperature is in excess of 500° C., the selectivity is decreased by the decomposition of the acid component, for example. On the other hand, if it is less than 200° C., the reaction is slow and the conversion tends to seriously drop. These are unsuitable for practical use.

In the process of the present invention, as described above, the addition of steam to the reaction system markedly increases the selectivity of the desired product. Although the exact reason for this is not clear, it is assumed as follows.

(1) The strong acid site on the catalyst surface which causes the decomposition of the reaction product, for example, and is disadvantageous for the reaction is collapsed by calcination with steam.

(2) The steam facilitates the release of the reaction product from the catalyst surface, thereby preventing the side reactions.

If the amount of steam added is too small, the above effects (1) and (2) are obtained only insufficiently and thus the selectivity cannot be increased. On the other hand, if it is too large, the concentration of the reaction product becomes too low, which is disadvantageous for the reaction.

The preferred amount of steam added is such that the molar ratio of water (steam)/acetic acid or propionic acid+formaldehyde is from 0.1/1 to 10/1. This ratio is hereinafter referred to as a "feed molar ratio" unless otherwise indicated.

The steam can be supplied by the following methods:

(I) The steam is introduced directly into the reaction system.

(II) Formaldehyde and/or acetic acid (propionic acid) is added as an aqueous solution.

(III) A combination of (I) and (II) above.

It is effective to carry out calcination with steam before the use of the catalyst because the selectivity can be maintained over a long period of time. This calcination with steam before the use of the catalyst can be carried out by passing steam along with air or inert gas through the solid catalyst layer and calcining it at a high temperature. In this case, it is preferred that the calcining temperature be from 200° to 700° C.

In a case that oxygen is added to the reaction system, air as well as pure oxygen can be used as the oxygen source. Air is desirable from an industrial standpoint. The amount of oxygen added is preferably from 0.5 to 20 vol %, more preferably from 1 to 12 vol % based on the total volume of the carrier gas and reactant vapor. It is preferred to add oxygen in such an amount that the reactant vapor does not form the oxygen composition falling within the explosion critical range.

In a case that the reaction is carried out in the presence of oxygen, the amount of the oxygen added can be calculated by the following equation:

$$\text{Amount of oxygen (vol \%)} = \frac{100 \times \text{coexisting air (ml/hr)} \times 0.2}{\text{nitrogen (ml/hr)} + \text{coexisting air (ml/hr)} + \text{reactant vapor (ml/hr)}}$$

The present invention is described in greater detail with reference to the following examples although it is not limited thereto. The conversion, selectivity, and yield are defined as follow:

$$\text{Conversion (\%)} = \frac{\text{Amount of formaldehyde consumed (moles)}}{\text{Amount of formaldehyde supplied (moles)}} \times 100$$

$$\text{Selectivity (\%)} = \frac{\text{Amount of AA, MA, MAA or MMA formed (moles)}}{\text{Amount of formaldehyde consumed (moles)}} \times 100$$

$$\text{Yield (\%)} = \frac{\text{Conversion (\%)} \times \text{selectivity (\%)}}{100}$$

AA is acrylic acid, MA is methyl acrylate, MAA is methacrylic acid, MMA is methyl methacrylate, and MA and MMA are products resulting from the reaction of methanol contained in formalin with the formed acrylic acid or methacrylic acid.

REFERENCE EXAMPLE

The acid strength of an acid site in the catalyst of the present invention was measured by the method described in Tanabe et al., Shokubai (Catalysts), 11, pages 210–216 (1969). This method is described below.

(1) The catalyst was ground in a mortar, and those passing through a 100 mesh screen (the size of mesh: 0.147 mm) were calcined at 500° C. for 2 hours in a stream of air.

(2) Immediately after calcining, the mass was placed in a desiccator, cooled to near room temperature, and stored in a sealed condition.

(3) About 10 ml of toluene was placed in each of 50 ml Erlenmeyer flasks the number of which was the same as that of indicators used. The toluene was previously distilled for dehydration by the use of sodium.

(4) The catalyst mass calcined in (2) above was measured in an amount of W g (about 0.2 to 0.3 g), and then placed in each Erlenmeyer flask.

(5) A 0.1% toluene solution of each indicator which had been previously prepared was added to each Erlenmeyer flask in an amount of about 0.3 ml. Immediately the catalyst mass exhibited an acidic or basic color. The indicators used are shown in Table 1 below.

TABLE 1

| Indicator | pKa of Conjugated Acid | Discoloration Basic - Acidic |
|---|---|---|
| p-nitrotoluene | −11.35 | Colorless - yellow |
| Anthraquinone | −8.2 | Colorless - yellow |
| Benzalacetophenone | −5.6 | Colorless - yellow |
| Dicinnamalacetone | −3.0 | Yellow - red |
| 4-Benzeneazodiphenylamine | +1.5 | Yellow - violet |
| p-Dimethylaminoazobenzene | +3.3 | Yellow - red |
| Methyl Red | +4.8 | Yellow - red |

(6) For the sample which exhibited an acidic color, a 1/10 N toluene solution of n-butylamine which had been previously prepared was dropped by the use of a microbiuret. The amount of the solution dropped until the acidic color disappeared was measured and expressed in terms of ml. The dropping interval was about 24 hours. The factor (f) of the 1/10 N toluene solution of n-butylamine was determined by titrating with a 1/10 N oxalic acid standard solution with phenolphthalein as an indicator.

(7) The acid amount was calculated as follows:

Assuming that the amount titrated when an indicator at $pKa = \alpha$ is added, is V ml, the acid amount A (mmol/g-Cat) at $pKa \leq \alpha$ can be represented by the following equation.

$$A = \frac{f \times V}{10 \times W}$$

wherein W is the amount of the catalyst (g), and f is the factor.

The acid strength distribution of the catalyst could be determined by measuring the acid amount using various indicators of different pKa according to the above-described procedure.

EXAMPLE 1

Silicaalumina (Al$_2$O$_3$ content: 28 wt %; acid amount at $pKa \leq -3.0$: 0.32 mmol/g-Cat) was impregnated in a 12 wt % aqueous boric acid solution (calculated as B$_2$O$_3$). The resulting mixture was vaporized to dry on a hot water bath, and the mass thus formed was dried overnight at 110° C. and then calcined at 400° C. for 2 hours in a stream of air to produce a B$_2$O$_3$-carried catalyst.

The acid amount at $pKa \leq -3.0$ of the above catalyst as measured by the above-described method was 0.35 mmol/g-Cat. About 1 g of the catalyst passing through a 32–48 mesh screen (the size of mesh: 0.295–0.495 mm) was placed in a reaction tube and heated to 400° C. in a stream of nitrogen for one hour after the temperature reached 400° C. Then, acetic acid and formalin (special grade chemical reagent) were introduced into the reaction tube to cause a gas phase reaction. The molar ratio of acetic acid/formaldehyde was 5/1, the reaction temperature was 350° C., and the SV was 1,850 ml/hr/ml-Cat. Products formed during the period of 30 to 90 minutes after the introduction of the reaction mixed gas was started, were analized by gas chromatography. The results were as follows:

Formaldehyde conversion: 58%
AA selectivity: 80%
MA selectivity: 3%
(AA+MA) yield: 48%

EXAMPLE 2

To a catalyst prepared by adding phosphorus oxide to TiO$_2$ (acid amount at $pKa \leq -3.0$: 0.01 mmol/g-Cat.) in a proportion of 15 wt % (calculated as P$_2$O$_5$) by the kneading method was further added boron oxide in a proportion of 10 wt % (calculated as B$_2$O$_3$) using a mixture of aqueous solution of boric acid and phosphoric acid according to the method of Example 1.

The acid amount at $pKa \leq -3.0$ of the catalyst thus produced was 0.10 mmol/g-Cat. Using this catalyst acetic acid and formalin were reacted under the same conditions as in Example 1 except that the SV was changed to 2,300 ml/hr/ml-Cat. The results were as follows:

Formaldehyde conversion: 44%
AA selectivity: 80%
MA selectivity: 3%
(AA+MA) yield: 37%

EXAMPLES 3 TO 6

To a catalyst prepared by adding phosphorus oxide to TiO$_2$ in a proportion of 8 wt % (calculated as P$_2$O$_5$) by the kneading method was further added boron oxide in a proportion of 15 wt % (calculated as B$_2$O$_3$) in the same manner as in Example 1.

The acid amount at $pKa \leq -3.0$ of the catalyst thus formed was 0.18 mmol/g-Cat. Using this catalyst, after the same pretreatment as in Example 1, acetic acid and formalin were reacted. The results and the reaction conditions are shown in Table 2.

TABLE 2

| | Example | | | |
|---|---|---|---|---|
| | 3 | 4 | 5 | 6 |
| Molar Ratio of Acetic Acid/Formaldehyde | 5/1 | 5/1 | 8/1 | 8/1 |
| Reaction Temperature (°C.) | 350 | 400 | 350 | 400 |
| SV (ml/hr/ml-Cat) | 2500 | 1250 | 1250 | 2500 |
| Formaldehyde Conversion (%) | 71 | 93 | 75 | 82 |
| AA Selectivity (%) | 82 | 56 | 75 | 83 |
| MA Selectivity (%) | 2 | 2 | 2 | 2 |
| (AA + MA) Yield (%) | 60 | 54 | 58 | 70 |

EXAMPLE 7

To γ-Al$_2$O$_3$ on the market was added boron oxide in a proportion of 10 wt % (calculated as B$_2$O$_3$) in the same manner as in Example 1.

The acid amount at $pKa \leq -3.0$ of the catalyst thus produced was 0.10 mmol/g-Cat. Using this catalyst acetic acid and formalin were reacted under the same conditions as in Example 1. The results were as follows:

Formaldehyde conversion: 38%
AA selectivity: 71%

MA selectivity: 2%
(AA+MA) yield: 28%

EXAMPLE 8

To a catalyst prepared by adding boron oxide in a proportion of 15 wt % (calculated as $B_2O_3$) to $Al_2O_3$ by the kneading method was further added boron oxide in a proportion of 12 wt % (calculated as $B_2O_3$) in the same manner as in Example 1.

The acid amount at $pKa \leq -3.0$ of the catalyst thus produced was 0.10 mmol/g-Cat. Using this catalyst acetic acid and formalin were reacted under the same conditions as in Example 2. The results are shown below.

Formaldehyde conversion: 43%
AA selectivity: 64%
MA selectivity: 1%
(AA+MA) yield: 28%

EXAMPLE 9

To a catalyst prepared by adding phosphorus oxide in a proportion of 12 wt % (calculated as $P_2O_5$) to $Al_2O_3$ by the kneading method was further added boron oxide in a proportion of 10 wt % (calculated as $B_2O_3$) in the same manner as in Example 1.

The acid amount at $pKa \leq -3.0$ of the catalyst thus produced was 0.50 mmol/g Cat. Using this catalyst acetic acid and formalin were reacted under the same conditions as in Example 2. The results are shown below.

Formaldehyde conversion: 43%
AA selectivity: 69%
MA selectivity: 2%
(AA+MA) yield: 31%

EXAMPLE 10

To $TiO_2$-$Al_2O_3$ ($TiO_2$ content: 14 wt %) prepared by the kneading method was added boron oxide in a proportion of 10 wt % (calculated as $B_2O_3$) in the same manner as in Example 1.

The acid amount at $pKa \leq -3.0$ of the catalyst thus produced was 0.33 mmol/g-Cat. Using this catalyst acetic acid and formalin were reacted under the same conditions as in Example 2. The results are shown below.

Formaldehyde conversion: 38%
AA selectivity: 64%
MA selectivity: 2%
(AA+MA) yield: 25%

EXAMPLE 11

To $ZrO_2$-$TiO_2$ ($ZrO_2$ content: 50 wt %) prepared by the kneading method was added phosphorus oxide in a proportion of 15 wt % (calculated as $P_2O_5$) using an aqueous solution of pyrophosphoric acid according to the method of Example 1.

The acid amount at $pKa \leq -3.0$ of the catalyst thus produced was 0.12 mmol/g-Cat. Using this catalyst, acetic acid and formalin were reacted under the same conditions as in Example 2. The results are shown below.

Formaldehyde conversion: 55%
AA selectivity: 66%
MA selectivity: 3%
(AA+MA) yield: 38%

EXAMPLE 12

To $ZrO_2$-$Al_2O_3$ ($ZrO_2$ content: 20 wt %) prepared by the kneading method was added boron oxide in a proportion of 10 wt % (calculated as $B_2O_3$) in the same manner as in Example 1.

The acid amount at $pKa \leq -3.0$ of the catalyst thus produced was 0.32 mmol/g-Cat. Using this catalyst, acetic acid and formalin were reacted under the same conditions as in Example 2. The results are shown below.

Formaldehyde conversion: 38%
AA selectivity: 47%
MA selectivity: 2%
(AA+MA) yield: 20%

COMPARATIVE EXAMPLE 1

Acetic acid and formalin were reacted under the same conditions as in Example 2 in the presence of a silica alumina catalyst ($Al_2O_3$ content: 13 wt %; acid amount at $pKa \leq -3.0$: 0.37 mmol/g-Cat). The results were as follows:

Formaldehyde conversion: 89%
AA selectivity: 60%
MA selectivity: 2%
(AA+MA) yield: 55%

The formation of MA is ascribable to the presence of methanol in formalin, and the amount of MA formed is small.

COMPARATIVE EXAMPLE 2

Acetic acid and formalin were reacted under the same conditions as in Example 1 in the presence of a silica alumina catalyst ($Al_2O_3$ content: 28 wt %; acid amount at $pKa \leq -3.0$: 0.32 mmol/g-Cat). The results were as follows:

Formaldehyde conversion: 78%
AA selectivity: 51%
MA selectivity: 2%
(AA+MA) yield: 41%

COMPARATIVE EXAMPLE 3

Acetic acid and formalin were reacted under the same conditions as in Example 2 in the presence of a catalyst (acid amount at $pKa \leq -3.0$: 0.63 mmol/g-Cat.) prepared by converting X-type zeolite into a proton-type catalyst using an aqueous solution of $NH_4Cl$. The results were as follows:

Formaldehyde conversion: 39%
AA selectivity: 36%
MA selectivity: 2%
(AA+MA) yield: 15%

COMPARATIVE EXAMPLE 4

Acetic acid and trioxane were reacted in the presence of the same silica alumina catalyst as used in Comparative Example 1 ($Al_2O_3$ content: 13 wt %). The molar ratio of acetic acid/trioxane was 5/1, the reaction temperature was 350° C., and the SV was 450 ml/hr/ml-Cat. The same pre-treatment as in Comparative Example 1 was applied. The results were as follows:

Trioxane conversion: 72%
AA selectivity: 53%
AA yield: 38%

COMPARATIVE EXAMPLE 5

Acetic acid and trioxane were reacted under the same conditions as in Example 2 in the presence of the same silica alumina catalyst as used in Comparative Example 2 ($Al_2O_3$ content: 28 wt %). The results were as follows:
Trioxane conversion: 48%
AA selectivity: 61%
AA yield: 29%

EXAMPLE 13

To $TiO_2$ with phosphorus oxide added in a proportion of 8 wt % (calculated as $P_2O_5$) by the kneading method were further added boron oxide and phosphorus oxide in proportions of 15 wt % and 10 wt % (calculated as $B_2O_3$ and $P_2O_5$, respectively) using a mixture of aqueous solutions of boric acid and phosphoric acid according to the method of Example 1.

The acid amount at $pKa \leq -3.0$ of the catalyst thus produced was 0.45 mmol/g-Cat. Propionic acid and formalin were reacted in the presence of the catalyst. The molar ratio of propionic acid/formaldehyde was 5/1, the reaction temperature was 350° C., the SV was 2,500 ml/hr/ml-Cat, and the same pretreatment as in Example 1 was applied. The results were as follows:
Formaldehyde conversion: 62%
MAA selectivity: 56%
MMA selectivity: 2%
(MAA+MMA) yield: 37%

COMPARATIVE EXAMPLES 6 TO 9

Acetic acid and formalin were reacted in the presence of each catalyst as shown in Table 2. The molar ratio of acetic acid/formalin was 5/1, the reaction temperature was 350° C., and the SV, the acid amount at $pKa \leq -3.0$ of each catalyst and the results are shown in Table 3.

TABLE 3

| Catalyst | COMPARATIVE EXAMPLE | | | |
|---|---|---|---|---|
| | 6 $\gamma$-$Al_2O_3$ | 7 $SiO_2$ | 8 $SiO_2$—MgO | 9 $SnO_2$ |
| Acid amount at $pKa \leq$ −3.0 (mmol/g-Cat) | 0.00 | 0.00 | 0.00 | 0.00 |
| SV (ml/hr/ml-Cat) | 2500 | 1800 | 1650 | 4500 |
| Formaldehyde Conversion (%) | 38 | 21 | 52 | 26 |
| AA Selectivity (%) | 14 | 7 | 2 | 2 |
| MA Selectivity (%) | 2 | — | 0.2 | 0.8 |
| (AA + MA) Yield (%) | 6 | 2 | 1 | 7 |

COMPARATIVE EXAMPLE 10

Acetic acid and formalin were reacted under the same conditions as in Example 1 in the presence of an X-type zeolite catalyst having only an acid site of acid strength, $+3.3 \leq pKa \leq +4.8$ and an acid amount at this acid strength of 0.07 mmol/g-Cat. The results were as follows:
Formaldehyde conversion: 31%
AA selectivity: 3.3%
MA selectivity: 0.1%
(AA+MA) yield: 1%

EXAMPLE 14

A catalyst prepared by adding phosphorus oxide in a proportion of 8 wt % (calculated as $P_2O_5$) to $TiO_2$ by the kneading method was impregnated with a mixed aqueous solution of boric acid and phosphoric acid. In the same manner as in Example 1, boron oxide and phosphorus oxide were added in proportions of 10 wt % and 10 wt % (calculated as $B_2O_3$ and $P_2O_5$), respectively.

The acid amount at $pKa \leq -3.0$ of the catalyst thus produced was 0.35 mmol/g-Cat, and the acid amount at $pKa < -11.35$ was 0 mmol/g-Cat. A catalyst fraction passing through a 32–48 mesh screen (the size of mesh: 0.295–0.495 mm) was packed in a reaction tube in an amount of about 1 g, heated to 350° C. in a stream of $N_2$ and steam, and calcined with steam for 1 hour. Thereafter, acetic acid and formalin (special grade chemicals reagent) were reacted in a gas phase. The molar ratio of acetic acid/formaldehyde was 5/1, the reaction temperature was 350° C., the SV was 2,650 ml/hr/ml-Cat, and the feed molar ratio was 2.3. Products formed during the period of 30 to 90 minutes after the introduction of the reaction mixed gas was started were analyzed by gas chromatography. The results were as follows:
AA selectivity: 92%
MA selectivity: 7%

The same procedure as above was repeated expect that steam was not used. The results were as follows:
AA selectivity: 77%
MA selectivity: 2%

EXAMPLE 15

To a catalyst prepared by adding phosphorus oxide in a proportion of 6 wt % (calculated as $P_2O_5$) to $TiO_2$ by the kneading method were further added boron oxide and phosphorus oxide in proportions of 10 wt % and 10 wt % (calculated as $B_2O_3$ and $P_2O_5$), respectively.

The acid amount at $pKa \leq -3.0$ of the catalyst thus produced was 0.32 mmol/g-Cat, and the acid amount at $pKa < -11.35$ was 0 mmol/g-Cat. Using this catalyst, acetic acid and formalin were reacted under the same conditions as in Example 14 except that the SV and the feed molar ratio were changed to 2,450 ml/hr/ml-Cat and 1.6, respectively. The results were as follows:
AA selectivity: 80%
MA selectivity: 3%

The above procedure as above was repeated except that steam was not used. The results were as follows:
AA selectivity: 75%
MA selectivity: 2%

EXAMPLE 16

To $ZrO_2$-$Al_2O_3$ ($ZrO_2$ content: 20 wt %) prepared by the kneading method was further added boron oxide in a proportion of 10 wt % (calculated as $B_2O_3$) using an aqueous solution of boric acid according to the method of Example 1.

The acid amount at $pKa \leq -3.0$ of the catalyst thus produced was 0.32 mmol/g-Cat, and the acid amount at $pKa < -11.35$ was 0 mmol/g-Cat. Using this catalyst, acetic acid and formalin were reacted under the same conditions as in Example 14 except that the steam calcining prior to the reaction was not applied, and the SV and the molar ratio of acetic acid/formalin were changed to 2,400 ml/hr/ml-Cat and 5/1, respectively.
The results were as follows:
AA selectivity: 78%
MA selectivity: 3%

The same procedure as above was repeated except that steam was not used. The results were as follows:
AA selectivity: 47%
MA selectivity: 2%

EXAMPLE 17

To a catalyst prepared by adding phosphorus oxide in a proportion of 10% (calculated as $P_2O_5$) to $TiO_2$ by the kneading method was further added boron oxide in a proportion of 10 wt % (calculated as $B_2O_3$) using an aqueous solution of boric acid according to the method of Example 1.

The acid amount at pKa≦ −3.0 of the catalyst thus produced was 0.27 mmol/g-Cat, and the acid amount at pKa< −11.35 was 0 mmol/g-Cat. Using this catalyst propionic acid and formalin were reacted. The molar ratio of propionic acid/formalin was 5/1, the reaction temperature was 350° C., the SV was 2,400 ml/hr/ml-Cat, and the same pretreatment as in Example 14 was applied. The results were as follows:

MAA selectivity: 84%
MMA selectivity: 3%

The same procedure as above was repeated except that steam was not used. The results were as follows:

MAA selectivity: 61%
MMA selectivity: 2%

EXAMPLE 18

$TiO_2$ with phosphorus oxide added in a proportion of 8 wt % (calculated as $P_2O_5$) by the kneading method was impregrated in a mixed aqueous solution of boric acid and phosphoric acid and, thereafter, processed in the same manner as in Example 1 to prepare a catalyst containing boron oxide and phosphorus oxide in proportions of 15 wt % and 10 wt % (calculated as $B_2O_3$ and $P_2O_5$), respectively, based on the total weight of the catalyst.

Figure 1:
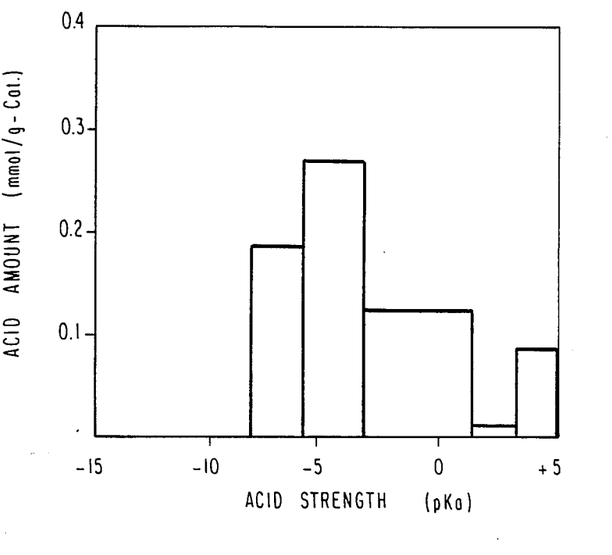

The acid amount at pKa≦ −3.0 of the catalyst was 0.45 mmol/g-Cat. The acid strength distribution of the solid catalyst as determined by the method described in Reference Example is shown in FIG. 1.

The catalyst was impregnated in an aqueous solution of ammonium molybdate and, thereafter, processed in the same manner as above to prepare a catalyst with molybdenum oxide added in a proportion of 2.8 wt % (calculated as $MoO_3$) (Mo element: 0.2 mmol/g-Cat).

About 1 g of the catalyst thus produced was packed in a reaction tube and heated to 350° C. in a stream of nitrogen for one hour after the temperature of 350° C. was reached, acetic acid and formalin (special grade chemical reagent) were introduced into the reaction and were reacted in a gas phase reaction. The molra ratio of acetic acid/ formaldehyde was 5/1, the reaction temperature was 350° C., and the SV was 2,600 ml/hr/ml-Cat.

Products formed during the period of 30 to 90 minutes after the introduction of the reaction mixed gas was started were analyzed by gas chromatography. The results were as follows:

Formaldehyde conversion: 58%
AA selectivity: 98%
MA selectivity: 1%
(AA+MA) yield: 57%

The formation of MA is ascribable to the presence of methanol in formalin, and the amount of MA formed is small.

The surface area of the catalyst used in the reaction was 95 m²/g-Cat. The surface area was measured by the BET one point method utilizing nitrogen adsorption using a $N_2$-He mixed gas (see, for example, *Shokubai Kogaku Koza*, 4 *Shokubai Kiso Sokuteiho*, Tijin Shokan Co., Ltd., pp. 50–67).

EXAMPLES 19 TO 23

The gas phase reaction of acetic acid and formalin was carried out under various conditions in the same manner as in Example 18 except that air was added to the reaction mixed gas. The reaction conditions and the results obtained are shown in Table 4.

The amount of carbonaceous residue deposited on the used catalyst was very small.

EXAMPLE 24

The same catalyst as used in Example 18 except that the molybdenum oxide content was changed to 7 wt % (calculated as $MoO_3$) (Mo element: 0.5 mmol/g-Cat) was used.

Acetic acid and formaldehyde were reacted for 30 hours in the same manner as in Example 18 except that air was added to the reaction mixed gas ($O_2$: 7.8 vol %).

The conversion, selectivity, and yield were determined after 1, 8, 20, or 30 hours passing from the start of the reaction, and the results are shown in Table 5. It can be seen from Table 5 that high activity could be maintained even after 30 hours. The deposition of carbonaceous residue responsible for the deterioration of catalytic activity was not observed at all in the used solid catalyst.

TABLE 4

|  | Example | | | | |
|---|---|---|---|---|---|
|  | 19 | 20 | 21 | 22 | 23 |
| Molar Ratio of Acetic acid/ Formaldehyde | 5/1 | 5/1 | 3/1 | 3/1 | 2/1 |
| Reaction Temperature (°C.) | 350 | 350 | 350 | 350 | 350 |
| SV (ml/hr/ml-Cat) | 2600 | 2550 | 2600 | 3450 | 2550 |
| Proportion of Oxygen added (vol %) | 6.6 | 3.5 | 3.5 | 2.5 | 3.6 |
| Formaldehyde Conversion (%) | 62 | 65 | 57 | 52 | 44 |
| Selectivity (%) | | | | | |
| AA | 84 | 85 | 95 | 98 | 96 |
| MA | 1 | 1 | 2 | 1 | 2 |
| Yield (%) | 53 | 56 | 55 | 51 | 43 |

TABLE 5

|  | Time (hr) | | | |
|---|---|---|---|---|
|  | 1 | 8 | 20 | 30 |
| Formaldehyde Conversion (%) | 57 | 66 | 70 | 74 |
| Selectivity (%) | | | | |
| AA | 98 | 98 | 97 | 87 |
| MA | 0.6 | 0.4 | 0.4 | 0.4 |
| Yield (%) | 56 | 65 | 68 | 65 |

Using the same catalyst as used above, acetic acid and formaldehyde were reacted in a gas phase under the same conditions as above except that air was not added. Products formed during the period of 3 hours after the start of the reaction were analyzed by gas chromatography.

The results were as follows:
Formaldehyde conversion: 65%
AA selectivity: 81%
MA selectivity: 2%
(AA+MA) yield: 54%

In the used catalyst, a large amount of carbonaceous residue deposited.

EXAMPLE 25

$TiO_2$ with phosphorus oxide added in a proportion of 10 wt % (calculated as $P_2O_5$) by the kneading method was impregnated with a mixture of a mixed aqueous solution of boric acid, phosphoric acid, an oxalic acid, and ammonium metavanadate and, thereafter, processed in the same manner as in Example 1 to prepare a solid catalyst containing 10 wt % of boron oxide (calculated as B$_2$O$_3$), 10 wt % of phosphorus oxide (calculated as P$_2$O$_5$), and 2.1 wt % of vanadium oxide (calculated as V$_2$O$_5$) (V element: 0.3 mmol/g-Cat).

Using the catalyst thus prepared, acetic acid and formalin were reacted under the same conditions as in Example 18 except that the reaction was carried out in the presence of air (O$_2$: 7.8 vol %) and SV was changed to 2,650 ml/hr/ml-Cat.

Products formed during the period of 30 to 90 minutes after the start of the reaction were analyzed by gas chromatography. The results were as follows:
 Formaldehyde conversion: 71%
 AA selectivity: 74%
 MA selectivity: 2%
 (AA+MA) yield: 54%

The amount of carbonaceous residue deposited on the used catalyst was very small.

The acid amount at pKa$\leq$ −3.0 of the catalyst when the vanadium oxide was not added was 0.39 mmol/g-Cat.

EXAMPLE 26

SiO$_2$-TiO$_2$ (SiO$_2$ content: 50 wt %) prepared by the kneading method was impregnated with a mixed aqueous solution of ammonium molybdate and boric acid and, thereafter, processed in the same manner as in Example 1 to prepare a catalyst containing 10 wt % of boron oxide (calculated as B$_2$O$_3$) and 7 wt % of molybdenum oxide (calculated as MoO$_3$) (Mo element: 0.5 mmol/g-Cat).

Using this catalyst, acetic acid and formalin were reacted under the same conditions as in Example 18. The results were as follows:
 Formaldehyde conversion: 46%
 AA selectivity: 85%
 MA selectivity: 1%
 (AA+MA) yield: 40%

The same procedure as above was repeated except that air was added (O$_2$: 11.3 vol %). The results were as follows:
 Formaldehyde conversion: 48%
 AA selectivity: 92%
 MA selectivity: 1%
 AA+MA yield: 45%

The amount of carbonaceous residue deposited on the used catalyst was very small. The acid amount at pKa$>$ −3.0 of the solid catalyst when the molybdenum oxide was not added was 0.15 mmol/g-Cat.

EXAMPLE 27

ZrO$_2$-TiO$_2$ (ZrO$_2$ content: 50 wt %) prepared by the kneading method was impregnated with a mixed aqueous solution of 12-molybdosilicic acid, ammonium metavanadate, and phosphoric acid and, thereafter, processed in the same manner as in Example 1 to prepare a catalyst containing 9.2 wt % of 12-molybdosilicic acid (Mo element: 0.05 mmol/g-Cat), 2.1 wt % of vanadium oxide (calculated as V$_2$O$_5$), (V element: 0.3 mmol/g-Cat), and 10 wt % of phosphorus oxide (calculated as P$_2$O$_5$).

Using this catalyst acetic acid and formalin were reacted under the same conditions as in Example 18 except that SV was changed to 2,670 ml/hr/ml-Cat. The results were as follows:
 Formaldehyde conversion: 76%
 AA selectivity: 68%
 MA selectivity: 1%
 (AA+MA) yield: 52%

The AA and MA selectivities based on acetic acid as calculated by the following equation were 52% and 1%, respectively.

Selectivity based on Acetic Acid (%) =

$$\frac{100 \times (\text{Amount of } AA, MA, MAA, \text{ or } MMA \text{ formed}) \text{ (moles)}}{\text{Amount of acetic acid consumed (moles)}}$$

The same procedure as above was repeated except that air (O$_2$: 4.7 vol %) was added. The results were as follows:
 Formaldehyde conversion: 67%
 AA Selectivity: 98%
 MA selectivity: 1%
 (AA+MA) yield: 66%
 AA selectivity based on acetic acid: 58%
 MA selectivity based on acetic acid: 1%

The amount of carbonaceous residue deposited on the used catalyst was very small.

The acid amount at pKa$\leq$ −3.0 of the catalyst when the 12-molybdosilic acid and vanadium oxide were not contained was 0.12 mmol/g-Cat.

EXAMPLE 28

TiO$_2$ with phosphorus oxide added in a proportion of 6 wt % (calculated as P$_2$O$_5$) by the kneading method was impregnated with a mixed aqueous solution of 12-molybdophosphoric acid, oxalic acid, ammonium metavanadate, cobalt nitrate and phosphoric acid and, thereafter, processed in the same manner as in Example 1 to prepare a catalyst containing 7.2 wt % of 12-molybdophosphoric acid (Mo element: 0.05 mmol/g-Cat), 2.2 wt % of vanadium oxide (calculated as V$_2$O$_5$) (V element: 0.3 mmol/g-Cat), 1.8 wt % of cobalt oxide (calculated as CoO) (Co element: 0.3 mmol/g-Cat), and 10 wt % of phosphorus oxide (calculated as P$_2$O$_5$).

Using this catalyst, acetic acid and formalin were reacted under the same conditions as in Example 1 except that the reaction was carried out in the presence of air (O$_2$: 6.4 vol %) and SV was changed to 2,550 ml/hr/ml-Cat. The results were as follows:
 Formaldehyde conversion: 84%
 AA selectivity: 87%
 MA selectivity: 1%
 (AA+MA) yield: 74%

The amount of the carbonaceous residue deposited on the used catalyst was very small.

The acid amount at pKa$\leq$ −3.0 of the catalyst when the 12-molybdophosphoric acid, vanadium oxide, and cobalt oxide were not contained was 0.14 mmol/g-Cat.

EXAMPLE 29

TiO$_2$ with phosphorus oxide added in a proportion of 8 wt % (calculated as P$_2$O$_5$) by the kneading method was impregnated with a mixed aqueous solution of boric acid and phosphoric acid and, thereafter, processed in the same manner as in Example 1 to prepare a catalyst containing 15 wt % of boron oxide (calculated as B$_2$O$_3$) and 10 wt % of phosphorus oxide (calculated as P$_2$O$_5$).

The acid amount at pKa$\leq$ −3.0 of the catalyst thus produced was 0.45 mmol/g-Cat.

This catalyst was further impregnated with a mixed aqueous solution of 12-molybdophosphoric acid and nickel nitrate and, thereafter, processed in the same manner as above to prepare a solid catalyst containing 8.2 wt % of 12-molybdophosphoric acid (Mo element: 0.05 mmol/g-Cat), and 2 wt % of nickel oxide (Ni element: 0.3 mmol/g-Cat).

Using the catalyst thus produced, acetic acid and formalin were reacted under the same conditions as in Example 18 except that air was added ($O_2$: 6.8 vol %). The results were as follows:
  Formaldehyde conversion: 72%
  AA selectivity: 88%
  MA selectivity: 1%
  (AA+MA) yield: 64%

The amount of the carbonaceous residue deposited on the used catalyst was very small.

EXAMPLE 30

$TiO_2$ with phosphorus oxide added in a proportion of 10 wt % (calculated as $P_2O_5$) by the kneading method was impregnated with a mixed aqueous solution of oxalic acid ammonium metavanadate, tin chloride, boric acid, and phosphoric acid and, thereafter, processed in the same manner as in Example 1 to prepare a catalyst containing 2.1 wt % of vanadium oxide (calculated as $V_2O_5$) (V element: 0.3 mmol/g-Cat), 3.1 wt % of tin oxide (calculated as SnO) (Sn element: 0.3 mmol/g-Cat), 10 wt % of boron oxide (calculated as $B_2O_3$), and 10 wt % of phosphorus oxide (calculated as $P_2O_5$).

Using the catalyst thus prepared, acetic acid and formalin were reacted under the same conditions as in Example 18 except that the reaction was carried out in the presence of air ($O_2$: 7.7 vol %) and SV was changed to 2,550 ml/hr/ml-Cat. The results were as follows:
  Formaldehyde conversion: 70%
  AA selectivity: 73%
  MA selectivity: 2%
  (AA+MA) yield: 53%
  AA selectivity based on acetic acid: 54%
  MA selectivity based on acetic acid: 2%

The amount of the carbonaceous residue deposited on the used catalyst was very small.

The acid amount at $pKa \leq -3.0$ of the catalyst when the vanadium oxide and tin oxide were not contained was 0.39 mmol/g-Cat.

EXAMPLE 31

Using the same catalyst as in Example 18, acetic acid and trioxane were reacted in the presence of air ($O_2$: 3.2 vol %). The molar ratio of acetic acid/trioxane was 9/1, the reaction temperature was 350° C., and SV was 2,550 ml/hr/ml-Cat. The results were as follows:
  Trioxane conversion: 86%
  AA selectivity: 63%
  AA yield: 54%

The amount of the carbonaceous residue deposited on the catalyst was very small.

EXAMPLE 32

$ZrO_2$-$Al_2O_3$ ($ZrO_2$ content: 20 wt %) prepared by the kneading method was impregnated with a mixed aqueous solution of oxalic acid, ammonium metavanadate and phosphoric acid, thereafter, processed in the same manner as in Example 1 to prepare a catalyst containing 1.8 wt % of vanadium oxide (calculated as $V_2O_5$) (V element: 0.3 mmol/g-Cat) and 9 wt % of phosphorus oxide (calculated as $P_2O_5$).

Using the catalyst thus prepared, propionic acid and formalin were reacted in the same manner as in Example 18. The molar ratio of propionic acid/formalin was 5/1, the reaction temperature was 350° C., and SV was 2,400 ml/hr/ml-Cat. The results were as follows:
  Propionic acid conversion: 68%
  MAA selectivity: 64%
  MMA selectivity: 2%
  (MAA+MMA) yield: 45%

The same procedure as above was repeated except that the reaction was carried out in the presence of air ($O_2$: 5.6 vol %). The results were as follows:
  Propionic acid conversion: 75%
  MAA selectivity: 63%
  MMA selectivity: 1%
  (MAA+MMA) yield: 48%

The amount of the carbonaceous residue deposited on the used catalyst was very small.

The acid amount at $pKa \leq -3.0$ of the solid catalyst when the vanadium oxide was not contained was 0.23 mmol/g-Cat.

The solid catalyst of the present invention has various advantages. Some of the major advantages are shown below.

(1) Activity is very high; both selectivity and conversion are satisfactory.

(2) If the reaction is carried out in the presence of steam, the selectivity is more increased and its high selectivity can be maintained for a long period of time.

(3) Thus acrylic acid or methacrylic acid can be produced from acetic acid or propionic acid and formaldehyde in high yield.

(4) The separation of the reaction product is very easy compared with the conventional methods.

(5) If the reaction is carried out in the presence of oxygen, high activity of the catalyst containing the oxidation ability-retaining compound can be maintained for a long period of time.

While the invention has been described in detail and with reference to specific embodiments thereof, it will be apparent to one skilled in the art that various changes and modifications can be made therein without departing from the spirit and scope thereof.

What is claimed is:

1. A process for producing arcylic acid or methacrylic acid by reacting acetic acid or propionic acid with formaldehyde in a gas phase in the presence of a solid catalyst containing at least one of boron oxide and phosphorus oxide and having an acid site of acid strength, $pka \leq -3.0$, said solid catalyst comprising
   (a) at least one compound selected from the group consisting of oxides or composite oxides of at least one element selected from the group consisting of Si, Al, Ti, Zr, Cd, Sm, Ga, Y and La;
   (b) at least one oxide selected from the group consisting of boron oxide and phosphorus oxide; and
   (c) at least one compound selected from the group consisting of (i) oxides of at least one element selected from the group consisting of V, Cr, Co, Ni, Mo, W and Pb, and (ii) heteropolyacids containing at least one polyatom selected from the group consisting of V, Mo and W.

2. The process as claimed in claim 1, wherein the boron oxide content (calculated as $B_2O_3$) of the solid catalyst is from 1 to 50 wt %.

3. The process as claimed in claim 1, wherein the phosphorus oxide content (calculated as $P_2O_5$) of the solid catalyst is from 1 to 50 wt %.

4. The process as claimed in claim 1, wherein the reacting is carried out in the presence of steam.

5. The process as claimed in claim 4, wherein the steam is added in such an amount that the molar ratio of water (steam)/acetic acid or propionic acid+formaldehyde falls within the range of 0.1/1 to 10/1.

6. The process as claimed in claim 1, wherein the acid strength, pKa, of the acid site of the solid catalyst is between −11.35 and −3.0.

7. The process as claimed in claim 1, wherein the solid catalyst comprises silica-alumina as a major component and boron oxide as component (b).

8. The process as claimed in claim 1, wherein the solid catalyst comprises titanium oxide, as a major component and boron oxide and phosphorus oxide as component (b).

9. The process as claimed in claim 1, wherein the solid catalyst comprises aluminum oxide as a major component and boron oxide or phosphorus oxide as component (b).

10. The process as claimed in claim 1, wherein the reacting is carried out in the presence of oxygen.

11. The process as claimed in claim 1, wherein the heteropolyacid contains at least one of P, B, and Si as a heteroatom.

12. The process as claimed in claim 1, wherein component (c) includes both at least one of the oxides and at least one of the heteropolyacids.

13. The process as claimed in claim 2, wherein the boron oxide content is from 5 to 30 wt %.

14. The process as claimed in claim 3, wherein the phosphorus oxide content is from 5 to 30 wt %.

15. The process as claimed in claim 1, wherein the amount of component (c) is from 0.01 to 10 mmol per gram of the catalyst.

16. The process as claimed in claim 15, wherein the amount of component (c) is from 0.03 to 5.0 mmol per gram of the catalyst.

* * * * *